(12) United States Patent
Parikh et al.

(10) Patent No.: US 11,833,138 B1
(45) Date of Patent: Dec. 5, 2023

(54) LIQUID PHARMACEUTICAL FORMULATIONS OF APIXABAN

(71) Applicant: TaP Pharmaceuticals, AG, Baar (CH)

(72) Inventors: Nilesh Parikh, Irvine, CA (US); William Hite, Winchester, CA (US)

(73) Assignee: TaP Pharmaceuticals AG, Baar (CH)

( * ) Notice: Subject to any disclaimer, the term of this patent is extended or adjusted under 35 U.S.C. 154(b) by 0 days.

(21) Appl. No.: 18/103,173

(22) Filed: Jan. 30, 2023

(51) Int. Cl.
*A61K 31/437* (2006.01)
*A61K 47/10* (2017.01)
*A61K 9/08* (2006.01)

(52) U.S. Cl.
CPC ............ *A61K 31/437* (2013.01); *A61K 47/10* (2013.01); *A61K 9/08* (2013.01)

(58) Field of Classification Search
CPC ............ A61K 31/437; A61P 9/00; A61P 9/10
USPC ........................................................ 514/303
See application file for complete search history.

(56) References Cited

U.S. PATENT DOCUMENTS

| 9,056,137 | B2 | 6/2015 | Hsu |
| 9,452,134 | B2 | 9/2016 | Badawy et al. |
| 11,304,912 | B2 | 4/2022 | Linn et al. |
| 2021/0299059 | A1 | 9/2021 | Liu et al. |

FOREIGN PATENT DOCUMENTS

| IN | 201621001853 | 10/2017 |
| WO | 2022031758 A1 | 2/2022 |
| WO | 2022123074 A1 | 6/2022 |

OTHER PUBLICATIONS

Bristol Meyers Sqibb. ELIQUIS® (apixaban) tablets. Sep. 2021, 15 pages.

*Primary Examiner* — Charanjit Aulakh
(74) *Attorney, Agent, or Firm* — John Burr

(57) ABSTRACT

Certain embodiments of the present disclosure provide liquid pharmaceutical formulations, suitable for oral administration, that contain glycerol and an amount of apixaban in the solution phase of the formulations of from 0.5 mg/ml to 6 mg/ml.

11 Claims, No Drawings

LIQUID PHARMACEUTICAL FORMULATIONS OF APIXABAN

FIELD

The instant disclosure provides liquid pharmaceutical formulations, suitable for oral administration, that comprise apixaban and that exhibit advantageous solubility properties therefor, and methods of making and using same.

BACKGROUND

Apixaban is an anticoagulant that functions as an inhibitor of trypsin-like serine protease enzymes, including factor Xa. Apixaban is the active pharmaceutical ingredient in ELIQUIS®tablets, approved by the United States Food and Drug Administration ("USFDA") and other regulatory authorities throughout the world. USFDA indications for ELIQUIS® include reducing the risk of stroke and systemic embolism in patients with nonvalvular atrial fibrillation, prophylaxis of deep vein thrombosis that may lead to pulmonary embolism in patients who have undergone hip or knee replacement surgery, treating deep vein thrombosis and pulmonary embolism, and reducing in the risk of recurrent deep vein thrombosis and pulmonary embolism following initial therapy.

Apixaban is a lactam containing compound and chemically described as 1-(4-methoxyphenyl)-7-oxo-6-[4-(2-oxopiperidin-1-yl)phenyl]-4,5,6, 7-tetrahydro1H-pyrazolo[3,4-c]pyridine-3-carboxamide with the molecular formula s $C_{25}H_{25}N_5O_4$. The chemical structure of apixaban is:

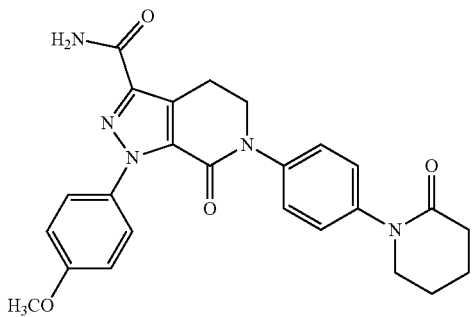 [SMILES: COc1ccc(-n2nc(C(N)=O)c3c2C(=O)N(c2ccc(N4CCCCC4=O)cc2)CC3)cc1]

U.S. Pat. No. 9,452,134 (the "'134 patent") teaches that apixaban has low aqueous solubility (i.e., 0.04 mg/ml) and identifies that as a major hurdle to the development of a liquid formulation of apixaban. The '134 patent recognizes that liquid formulations are important for administration of apixaban to the pediatric population and to adults who are unable to swallow a solid dosage form. The '134 patent determined that a concentration of 0.4 mg/ml of apixaban in an oral liquid formulation adequately supports a desired dosage range of from 0.04 mg to 5.0 mg with administered volumes ranging from 0.10 ml to 12.5 ml (i.e., volumes that can be both accurately measured and conveniently administered). The '134 patent states that a minimum solubility of apixaban of 0.50 mg/ml at 15-25° C. can provide a robust formulation at the 0.4 mg/mL target concentration. Since such solubility would help to maintain apixaban in a dissolved state within the range of temperatures to which the formulation may be exposed during shipping and handling by patients. The '134 patent discloses that its liquid formulations of apixaban comprise a vehicle in which the solubility of apixaban is at least 0.50 mg/ml. The '134 patent teaches that its vehicle for apixaban contains water and at least two solubilizers that are selected from the group consisting of a non-ionic surfactant, an ionic surfactant, a hydrophilic polymer, ethanol, a polyhydric alcohol, a polyethylene glycol, and a carbohydrate.

The '134 patent describes non-ionic surfactants as non-ionizable, surface-active agents that reduce the surface tension of a liquid and thus allows it to foam or wet a solid. Examples of non-ionic surfactants for use in apixaban liquid formulations taught by the '134 patent are polysorbates, poloxamers, polyoxyethylene castor oil derivatives, polyoxyglycerides, vitamin E polyethylene glycol succinate, and macrogol 15 hydroxy stearate. The '134 patent describes ionic surfactants as surface-active agents with ionizable group(s) which reduce the surface tension of a liquid and thus allows it to foam or wet a solid. Examples of ionic surfactants for use in apixaban liquid formulation taught by the '134 patent are sodium lauryl sulfate and docusate sodium.

The '134 patent describes hydrophilic polymers as high molecular weight compounds derived from the addition of many smaller units and having a strong affinity for water. Examples of hydrophilic polymers for use in the apixaban liquid formulation taught by the '134 patent are povidone, copovidone, hydroxypropyl cellulose, and hydroxypropyl methylcellulose. The '134 patent describes polyhydric alcohols as compounds with more than one hydroxyl group. Examples of polyhydric alcohols for use in the apixaban liquid formulation taught by the '134 patent are glycerin, propylene glycol, sorbitol, and mannitol.

The '134 patent describes polyethylene glycol as polymers of ethylene glycol formed by the reaction of ethylene oxide and water. Examples of polyethylene glycols for use in the apixaban liquid formulation taught by the '134 patent are polyethylene glycol 200, 300, and 400. The '134 patent describes carbohydrates as a class of organic compounds that are polyhydroxy aldehydes or ketones. Examples of carbohydrates that for use in the apixaban liquid formulation taught by the '134 patent are fructose, sucrose, and lactose.

International Patent Cooperation Treaty Publication WO2022/123074 ("the '074 publication") teaches that liquid medicaments intended for the oral administration are advantageously administered in small dose volumes of less than 10 ml, especially for geriatric, pediatric, or bedridden patients, e.g. patients undergoing hip surgery and for patients who usually receive their medication through feeding tubes. The '074 publication teaches pharmaceutical formulations suitable for oral administration that contain apixaban at concentrations within the range of 0.25 mg/ml to 10 mg/ml and that have as a dose volume of equal to or less than: 10 ml, 5 ml, 4 ml, 3 ml, 2 ml, or 1 ml. The '074 publication teaches that such apixaban formulations which also contain propylene glycol in amounts of more than: 35% (w/v), 40% (w/v), 45% (w/v), 50% (w/v), or 55% (w/v), based on the total formulation, dissolves apixaban in small vehicle volumes, resulting in a solution which remains stable and is free of precipitation/crystallization.

The '074 publication teaches that its Example Formulations 16-20 comprise, in 100% propylene glycol, apixaban in the following concentrations, respectively: 0.25 mg/ml, 0.5 mg/ml, 1.0 mg/ml, 1.5 mg/ml, 1.85 mg/ml, and 2.0 mg/ml. The '074 publication teaches that, at 20° C., the apixaban is soluble in its Example Formulations 16-19 (i.e., up to 1.85 mg/ml apixaban) and that, at 20° C., the apixaban is partially soluble in its Example Formulation 20 (i.e., 2.0 mg/ml apixaban). (See Table 1 of the '074 publication, which for ready reference is reproduced below as Table A.) The '074 publication also teaches that its Example Formulations 7-11 comprise, in 35% propylene glycol and 60% glycerol, apixaban in the following concentrations, respectively: 0.25 mg/ml, 0.5 mg/ml, 1.0 mg/ml, 1.5 mg/ml, and 2.0 mg/ml. The '074 publication teaches that, at 20° C., the apixaban is soluble in its Example Formulations 7 and 8 (i.e., up to 0.5 mg/ml apixaban) and that, at 20° C., the apixaban is partially soluble in its Example Formulation 9 (i.e., 1.0 mg/ml apixaban) and that, at 20° C., the apixaban is in soluble in its Example Formulations 9 and 11 (i.e., 1.5 mg/ml and 2.0 mg/ml apixaban, respectively). (See Table 1 of the '074 publication, which for ready reference is reproduced below as Table A.) The '074 publication therefore teaches that the solubility of apixaban is essentially cut in half in formulations that contain 60% glycerol and 35% propylene glycol as compared to formulations that contain no glycerol and 100% propylene glycol.

TABLE A

The '074 publication's example 7-38 apixaban compositions, solubilities

| Example No | Formulation | Concentration (mg/ml) | Temp (° C.) | Remarks |
|---|---|---|---|---|
| 7 | Apixaban + 35% Propylene Glycol + 60% Glycerol anh. | 0.25 | 20 | Soluble |
| 8 | Apixaban + 35% Propylene Glycol + 60% Glycerol anh. | 0.5 | 20 | Soluble |
| 9 | Apixaban + 35% Propylene Glycol + 60% Glycerol anh. | 1.0 | 20 | Partially soluble |
| 10 | Apixaban + 40% Propylene Glycol + 60% Glycerol anh. | 1.5 | 20 | Insoluble |
| 11 | Apixaban + 40% Propylene Glycol + 60% Glycerol anh. | 2.0 | 20 | Insoluble |
| 12 | Apixaban + 40% Propylene Glycol + 60% Glycerol anh. | 1.0 | 35 | Partially soluble |
| 13 | Apixaban + 40% Propylene Glycol + 60% Glycerol anh. | 1.0 | 40 | Soluble |
| 14 | Apixaban + 40% Propylene Glycol + 60% Glycerol anh. | 1.5 | 45 | Soluble |
| 15 | Apixaban + 40% Propylene Glycol + 60% Glycerol anh. | 2.0 | 45 | Soluble |
| 16 | Apixaban + 100% Propylene Glycol | 0.25 | 20 | Soluble |
| 17 | Apixaban + 100% Propylene Glycol | 0.5 | 20 | Soluble |
| 18 | Apixaban + 100% Propylene Glycol | 1.0 | 20 | Soluble |
| 19 | Apixaban + 100% Propylene Glycol | 1.85 | 20 | Soluble |
| 20 | Apixaban + 100% Propylene Glycol | 2.00 | 20 | Partially soluble |
| 21 | Apixaban + 100% Propylene Glycol | 2.50 | 35 | Soluble |
| 22 | Apixaban + 100% Propylene Glycol | 3.33 | 35 | Soluble |
| 23 | Apixaban + 100% Propylene Glycol | 5.00 | 45 | Soluble |
| 24 | Apixaban + 100% Propylene Glycol | 10.00 | 55 | Soluble |
| 25 | Apixaban + 40% Propylene Glycol + 3% PEG-200 + 57% Glycerol anh. | 0.25 | 20 | Soluble |
| 26 | Apixaban + 40% Propylene Glycol + 3% PEG-200 + 57% Glycerol anh. | 0.5 | 20 | Soluble |
| 27 | Apixaban + 97% Propylene Glycol + 3% PEG-200 | 3.00 | 20 | Soluble |
| 28 | Apixaban + 97% Propylene Glycol + 3% PEG-200 | 3.33 | 20 | Partially soluble |
| 29 | Apixaban + 97% Propylene Glycol + 3% PEG-200 | 3.33 | 35 | Soluble |
| 30 | Apixaban + 97% Propylene Glycol + 3% PEG-200 | 5.00 | 20 | Partially soluble |
| 31 | Apixaban + 97% Propylene Glycol + 3% PEG-200 | 5.00 | 20 | Partially soluble |
| 32 | Apixaban + 97% Propylene Glycol + 3% PEG-200 | 5.00 | 45 | Soluble |
| 33 | Apixaban + 45% Propylene Glycol + 55% Sorbitol solution | 5.00 | 35 | Partially soluble |
| 34 | Apixaban + 45% Propylene Glycol + 55% Sorbitol solution | 5.00 | 45 | Soluble |
| 35 | Apixaban + 45% Propylene Glycol + 55% Fructose solution | 5.00 | 35 | Partially soluble |
| 36 | Apixaban + 45% Propylene Glycol + 55% Fructose solution | 5.00 | 45 | Soluble |
| 37 | Apixaban + 45% Propylene Glycol + 55% Maltitol solution | 5.00 | 35 | Partially soluble |
| 38 | Apixaban + 45% Propylene Glycol + 55% Maltitol solution | 5.00 | 45 | Soluble |

SUMMARY

Certain embodiments of the disclosure provide liquid pharmaceutical formulations, suitable for oral administration, that contain a therapeutically effective amount of apixaban; and an amount of glycerol sufficient to result in from 0.5 mg/ml to 1.75 mg/ml of the apixaban being in the solution phase of the formulation, at 20 hours after the formulation's manufacture when the formulation is kept at 25° C.±2° C. Some of such embodiments are free of added: polysorbate, povidone, hydroxypropyl cellulose, or hydroxypropyl methylcellulose; propylene glycol, sorbitol, mannitol, fructose, sucrose, and lactose. In some of such embodiments the amount of apixaban in the solution phase of the formulation is from 0.75 mg/ml to 1.75 mg/m, from 1.0 mg/ml to 1.75 mg/ml, or 1.0 mg/ml. In some of such embodiments the amount of glycerol is from 370 mg/ml to 1260 mg/ml, from 462.5 mg/ml to 1260 mg/ml, from 740 mg/ml to 1260 mg/ml, or 1260 mg/ml. In some of such embodiments the formulations are free of added surfactant, hydrophilic polymer, polyhydric alcohol other than the glycerol, and carbohydrate.

Certain embodiments of the present disclosure provide methods of (i) reducing the risk of stroke and systemic embolism in patients with nonvalvular atrial fibrillation, (ii) reducing the risk of deep vein thrombosis leading to pulmonary embolism in patients who have undergone hip or knee replacement surgery, (iii) treating deep vein thrombosis and pulmonary embolism, or (iv) treating recurrent deep vein thrombosis and pulmonary embolism, that include the step of orally administering a formulation of the disclosure to a subject presenting nonvalvular atrial fibrillation, deep vein thrombosis or pulmonary embolism or who has undergone hip or knee replacement therapy. In some of such embodiments, the formulation is administered to the subject once daily and wherein the formulation contains a total amount of apixaban of from 1 mg to 10 mg.

Certain embodiments of the present disclosure provide methods for preparing liquid formulations of apixaban that involve adding glycerol to a vessel with stirring or other mixing and heating to 80° C. ±5° C.; adding apixaban to the glycerol with continued stirring or other mixing at 80° C.±5° C. and cooling the mixture with continued stirring until the resulting suspension of apixaban in glycerol reaches 55° C. (at least one hour) and becomes a clear solution; and allowing the resultant solution to stand and cool to room temperature (25° C±2° C.).

Exemplary embodiment A.1 of the disclosure provides a liquid pharmaceutical formulation, suitable for oral administration, that contains a therapeutically effective amount of apixaban; and an amount of glycerol sufficient to result in from 0.5 mg/ml to 1.70 mg/ml of the apixaban being in the solution phase of the formulation, at 24 hours after the formulation's manufacture when the formulation is kept at 25° C.±2° C. Embodiment A.1 is free of added: polysorbate, povidone, hydroxypropyl cellulose, or hydroxypropyl methylcellulose; propylene glycol, sorbitol, mannitol, fructose, sucrose, and lactose. Exemplary embodiments A.2, A.3, and A.4 differ from embodiment A.1 by containing in their solution phase, respectively, from 0.75 mg/ml to 1.70 mg/ml apixaban, from 1.0 mg/ml to 1.70 mg/ml apixaban, or 1.0 mg/ml apixaban. Exemplary embodiments A.5, A.6, A.7, and A.8 differ from embodiments A.1-A.4 by containing, respectively, glycerol in an amount of from 370 mg/ml to 1260 mg/ml, from 462.5 mg/ml to 1260 mg/ml, from 740 mg/ml to 1260 mg/ml, or 1260 mg/ml. Exemplary embodiment A.9 differs from embodiments A.1-A.8 by being free of added surfactant, hydrophilic polymer, polyhydric alcohol other than the glycerol, and carbohydrate.

Exemplary embodiment B.1 of the disclosure provides a liquid pharmaceutical formulation, suitable for oral administration, that contains from 462.5 mg/ml to 1260 mg/ml glycerol and from 0.75 mg/ml to 1.75 mg/ml apixaban that is at least 95% in the solution phase of the formulation, at 20 hours after the formulation's manufacture when the formulation is kept at 25° C.±2° C. Embodiment B.1 is free of added: polysorbate, povidone, hydroxypropyl cellulose, or hydroxypropyl methylcellulose; and of propylene glycol, sorbitol, mannitol, fructose, sucrose, and lactose. Exemplary embodiments B.2, B.3, and B.4 differ from embodiment B.1 by containing in their solution phase, respectively, from 1.0 mg/ml to 1.70 mg/ml apixaban, from 1.0 mg/ml to 1.25 mg/ml apixaban, or 1.0 mg/ml apixaban, at least 97% of such amounts of apixaban being in the solution phase of the formulations. Exemplary embodiments B.5 and B.6 differ from embodiments B.1-B.4 by containing, respectively, glycerol in an amount of from 740 mg/ml to 1260 mg/ml or 1260 mg/ml. Exemplary embodiments B.7, B.8, and B.9 differ from embodiments B.1-B.6 by containing, respectively, at least 98% or at least 99% of the apixaban in solution. Exemplary embodiment B.10 differs from embodiments B.1-B.9 by being free of added surfactant, hydrophilic polymer, polyhydric alcohol other than the glycerol, and carbohydrate.

Exemplary embodiment C.1 of the disclosure provides a liquid pharmaceutical formulation, suitable for oral administration, that contains from 462.5 mg/ml to 1260 mg/ml glycerol and from 0.75 mg/ml to 1.70 mg/ml apixaban that is at least 95% in the solution phase of the formulation, at 24 hours after the formulation's manufacture when the formulation is kept at 25° C.±2° C. Embodiment C.1 is free of added: polysorbate, povidone, hydroxypropyl cellulose, or hydroxypropyl methylcellulose; and of propylene glycol, sorbitol, mannitol, fructose, sucrose, and lactose. Exemplary embodiments C.2, C.3, and C.4 differ from embodiment C.1 by containing in their solution phase, respectively, from 1.0 mg/ml to 1.70 mg/ml apixaban, from 1.0 mg/ml to 1.25 mg/ml apixaban, or 1.0 mg/ml apixaban, at least 97% of such amounts of apixaban being in the solution phase of the formulations. Exemplary embodiments C.5 and C.6 differ from embodiments C.1-C.4 by containing, respectively, glycerol in an amount of from 740 mg/ml to 1260 mg/ml or 1260 mg/ml. Exemplary embodiments C.7, C.8, and C.9 differ from embodiments C.1-C.6 by containing, respectively, at least 98% or at least 99% of the apixaban in solution. Exemplary embodiment C.10 differs from embodiments C.1-C.9 by being free of added surfactant, hydrophilic polymer, polyhydric alcohol other than the glycerol, and carbohydrate. Certain embodiments of the present disclosure provide methods of (i) reducing the risk of stroke and systemic embolism in patients with nonvalvular atrial fibrillation, (ii) reducing the risk of deep vein thrombosis leading to pulmonary embolism in patients who have undergone hip or knee replacement surgery, (iii) treating deep vein thrombosis and pulmonary embolism, or (iv) treating recurrent deep vein thrombosis and pulmonary embolism, that include the step of orally administering a formulation according to any one of exemplary embodiments A.1-A.8, B.1-B.10, or C.1-C.10 of the disclosure to a subject presenting nonvalvular atrial fibrillation, deep vein thrombosis or pulmonary embolism or who has undergone hip or knee replacement therapy. In some of such embodiments, the formulation is administered to the subject once daily and wherein the formulation contains a total amount of apixaban of from 1 mg to 10 mg.

Certain embodiments of the disclosure provide liquid pharmaceutical formulations, suitable for oral administration, that contain a therapeutically effective amount of apixaban; and at least 60% w/v glycerol. In such formulations, from 0.75 mg/ml to 1.75 mg/ml of the apixaban is in the solution phase of the formulation, at 20 hours after the formulation's manufacture when the formulation is kept at 25° C.±2° C. In some of such formulations, the amount of apixaban in the solution phase of the formulation is from 1.0 mg/ml to 1.75 mg/ml. or 1.0 mg/ml. Some of such formulations contain at least 70% glycerol, at least 80% glycerol, at least 90% glycerol, at least 95% glycerol, at least 97%, at least 99% glycerol, or the apixaban and balance glycerol.

DETAILED DESCRIPTION

The present disclosure provides liquid pharmaceutical formulations of apixaban that are suitable for oral administration and that exhibit surprisingly advantageous high levels of apixaban solubilities not attainable prior to the instant disclosure. Such formulations of the disclosure are useful for reducing the risk of stroke and systemic embolism in patients with nonvalvular atrial fibrillation, the prophylaxis of deep vein thrombosis that may lead to pulmonary embolism in patients who have undergone hip or knee replacement surgery, treating deep vein thrombosis and pulmonary embolism, and reducing in the risk of recurrent deep vein thrombosis and pulmonary embolism following initial therapy.

In some formulations of the disclosure, the proportion of apixaban in the solution phase can be from 75% to 99%, from 80% to 99%, from 85% to 99%, from 90% to 99%, or from 95% to 99%. In some formulations of the disclosure, the proportion of apixaban in the solution phase can be from 75% to 98%, from 80% to 98%, from 85% to 98%, from 90% to 98%, or from 95% to 98%. In some formulations of the disclosure, the proportion of apixaban in the solution phase can be from 75% to 97%, from 80% to 97%, from 85% to 97%, from 90% to 97%, or from 95% to 97%.

Formulations as disclosed herein can "comprise" a list of ingredients, such list then being open to inclusion of further unspecified ingredients. Alternatively, formulations as disclosed herein can "consist of" a list of ingredients, meaning that the formulations include only the listed ingredients. Or, formulations as disclosed herein can "consist essentially of" the listed ingredients, meaning that the formulations include all of the listed ingredients, and may include as well any further ingredients that do not materially affect the utility of the formulation.

For purposes of this disclosure, such utility is the maintaining of a high concentration of apixaban in solution and a high proportion of the apixaban in a formulation being in the solution phase.

In some embodiments, formulations of the present disclosure contain apixaban, at concentrations in the overall formulation of from 0.5 mg/ml to 30 mg/ml and further exemplary concentrations include 0.5 mg/ml, 0.75 mg/ml, 1 mg/ml, 1.25 mg/ml, 1.5 mg/ml, 1.75 mg/ml, 2 mg/ml, 2.5 mg/ml, 3 mg/ml, 3.5 mg/ml, 4 mg/ml, 4.5 mg/ml, 5 mg/ml, 5.5 mg/ml or 6 mg/ml as well as ranges between any two of said apixaban concentrations.

In some embodiments, formulations of the present disclosure contain apixaban, at concentrations in the solution phase of the formulation of from 0.5 mg/ml to 3 mg/ml and exemplary particular concentrations include 0.5 mg/ml, 0.75 mg/ml, 1 mg/ml, 1.25 mg/ml, 1.5 mg/ml, 1.75 mg/ml, 2 mg/ml, 2.5 mg/ml, 3 mg/ml, as well as ranges between any two of said apixaban in solution phase concentrations.

In some embodiments, formulations of the disclosure have a proportion of the overall amount of apixaban present in the formulation that is dissolved (i.e., in solution) which is 70%, 75%, 80%, 85%, 90%, 91%, 92%, 93%, 94%, 95%, 96%, 97%, 98%, 99%, 100%, or in a range between any two of such proportions.

In some embodiments as described above, a formulation of the disclosure can consist of the apixaban and glycerol. In some embodiments, a formulation of the disclosure can consist of the apixaban, glycerol and a pH adjusting agent as described below. In any such embodiments, the pH of the formulation can be from 6 to 11 as described below. In some embodiments, a formulation of the disclosure can consist of the apixaban, glycerol, a pH adjusting agent as described below and one or more of a sweetener, flavorant, polymer, surfactant, tonicity agent and preservative as described below.

Glycerols useful in formulations of the disclosure include glycerol USP Grade (1,2,3-Propanetriol), a colorless, odorless liquid available at a minimum 96.0% or a minimum 99.5% glycerol by assay. Commercially available glycerols include 99.9% glycerol by Puratin, 99.7% glycerol by Optim, 100% glycerol by JT Baker, 99.5% glycerol by MP Biomedicals, 99.4% glycerol by Honeywell, 99.8% glycerol by VWR Scientific, 99% glycerol by Spectrum, 100% glycerol by Millipore Sigma, 99% glycerol by Bean Town Chemical, 99.9% glycerol by Thermofischer Scientific Chemicals, 99.8% glycerol by Arcos Chemicals, 99.8% glycerol by VWR International. Also useful in formulations of the disclosure are glycerol esters that include glyceryll (2 ethylhexyl) oleate, glycerol trioleate, glyceryl monooleate, and glyceryl monotallate.

In some embodiments, formulations of the disclosure can include a sweetener. Sweeteners useful in the formulations of the present disclosure include acesulfame-K, advantame, alitame, aspartame, brazzein, carrelame, curculin, cyclamic acid, corn syrup (e.g., high fructose corn syrup), cyclamate, dihydrochalchone, erythritol, fructose, galactose, glucose, glycerin, glycine, glycyrrhizic acid, hydrogenated glucose syrup, hydrogenated starch hydrolysate, isomalt, lactitol, lactose, mabilin, miraculin, maltitol, maltodextrin, maltose, monatin, mannitol, mannose, mogrosides, monellin, neohesperidin, pentadin, saccharin, sorbitol, stevia glycosides, sucralose, sucrose, tagatose, tryptophan, and xylitol. The sweetener may be present in liquid pharmaceutical formulations of the disclosure in weight to volume proportions of 0.10% w/v, 0.15% w/v, 0.20% w/v, 0.25% w/v, 0.30% w/v, 0.3 5% w/v, 0.40% w/v, 0.45% w/v, 0.50% w/v, 0.55% w/v, 0.60% w/v, 0.65% w/v, 0.70% w/v 0.75% w/v, 0.80% w/v, 80.5% w/v, 0.90% w/v, 0.95% w/v, 1% w/v, 2% w/v, 3% w/v, 4% w/v, 5% w/v, 6% w/v, 7% w/v, 8% w/v, 9% w/v, 10% w/v or in a range between any two of said sweetener proportions. The formulations may comprise combinations of sweeteners, in amounts that individually or in aggregate achieve(s) the stated weight to volume proportions.

In some embodiments, formulations of the disclosure can include a flavorant. Flavorants useful in the formulations of the present disclosure include chocolate, vanilla, caramel, orange, lemon, lime, strawberry, raspberry, blueberry, cherry, cinnamon, and nutmeg. The flavorant may be present in liquid pharmaceutical formulations of the disclosure in weight to volume proportions of 0.10% w/v, 0.15% w/v, 0.20% w/v, 0.25% w/v, 0.30% w/v, 0.35% w/v, 0.40% w/v, 0.45% w/v, 0.50% w/v, 0.55% w/v, 0.60% w/v, 0.65% w/v, 0.70% w/v 0.75% w/v, 0.80% w/v, 80.5% w/v, 0.90% w/v, 0.95% w/v, 1% w/v, 2% w/v, 3% w/v, 4% w/v, 5% w/v, 6% w/v, 7% w/v, 8% w/v, 9% w/v, 10% w/v or in a range between any two of said flavorant proportions. The formulations may comprise combinations of flavorant, in amounts that individually or in aggregate achieve(s) the stated weight to volume proportions.

In some embodiments, formulations of the disclosure can contain a pH adjusting agent and/or a buffer. Acidic pH adjusting agents useful in formulations of the disclosure include fumaric acid, formic acid, acetic acid, trichloroacetic acid, benzoic acid, oxalic acid, hydrofluoric acid, hydrogen sulfide, nitrous acid, sulfurous acid, phosphoric acid, and combinations thereof. Alkaline pH adjusting useful in formulations of the disclosure include sodium hydroxide, potassium hydroxide, calcium hydroxide, ammonium carbonate, ammonium hydroxide, ethanolamine, and trolamine. Buffers useful in formulations of the disclosure include acetic acid, sodium acetate, benzoic acid, sodium benzoate, boric acid, sodium borate, citric acid, sodium citrate, sodium phosphate, monobasic sodium phosphate, dibasic sodium phosphate, potassium phosphate, monobasic potassium phosphate, dibasic potassium phosphate, sodium acetate, lactic acid, a tartaric acid, sodium tartrate, sodium bicarbonate, sodium carbonate, tris(hydroxymethyl)aminomethane ("TRIS"), or a combination thereof In such formulations, the buffer and/or pH adjusting agent are present in the formulations in amounts, alone or together, that are sufficient to cause the formulation to have a pH of from 6 to 11, for example pH 6, pH 6.1, pH 6.2, pH 6.3, pH 6.4, t pH 6.5, pH 6.6, pH 6.7, pH 6.8, pH 6.9, pH 7, pH 7.1, pH 7.2, pH 7.3, pH 7.4, pH 7.5, pH 7.6, pH 7.7, pH 7.8, pH 7.9, pH 8, pH 8.1, pH 8.2, pH 8.3, pH 8.4, pH 8.5, pH 8.6, pH 8.7, pH 8.8, pH 8.9, pH 9, pH 9.1, pH 9.2, pH 9.3, pH 9.4, pH 9.5, pH 9.6, pH 9.7, pH 9.8, pH 9.9, pH 10, pH 10.1, pH 10.2, pH 10.3, pH 10.4, pH 10.5, pH 10.6, pH 10.7, pH 10.8, pH 10.9, pH 11, as well as in a range between any two such pH values.

In some embodiments, formulations of the present disclosure are pourable. The viscosities of such formulations can range from 1 centipoise ("cps") (i.e., the viscosity of water at room temperature) to 25,000 cps (i.e., the viscosity of chocolate syrup at room temperature); and exemplary particular viscosities of formulations of the disclosure include 1 cps, 25 cps, 50 cps, 75 cps, 100 cps, 150 cps, 200 cps (about the viscosity of maple syrup at room temperature), 250 cps, 300 cps, 400 cps, 500 cps, 600 cps, 700 cps, 800 cps, 900 cps, 1000 cps (about the viscosity of glycerin at room temperature), 1100 cps, 1200 cps, 1300 cps, 1400 cps, 1500 cps, 1600 cps, 1700 cps, 1800 cps, 1900 cps, 2000 cps, 2100 cps, 2200 cps, 2300 cps, 2400 cps, 2500 cps, 2600 cps, 2700 cps, 2800 cps, 2900 cps, 3000, 3500 cps, 4000 cps, 4500 cps, 5000 cps, 6000 cps, 7000 cps, 8000 cps, 9000 cps, 10,000 cps, 12,500 cps, 15,000 cps, 17,500 cps, 20,000, cps 22,500 cps, 25,000 cps (about the viscosity of chocolate syrup at room temperature), 27,500 cps, 30,000, cps as well as in a range between any two of said viscosities.

In some embodiments, formulations of the disclosure can contain a polymer. Non-ionic polymers useful in certain formulations of the disclosure include hydroxyethyl cellulose, hydroxypropylmethyl cellulose, methyl cellulose, carboxymethyl cellulose, polyvinyl pyrrolidone, and polyvinyl alcohol. Ionic polymers useful in certain formulations of the disclosure include polyacrylates (e.g., carbopols and carbomers), alginates, chitosans, hyaluronic acid, and xanthan gum. Such ionic and/or nonionic polymers may be present in formulations of the disclosure in weight to volume proportions of the overall formulation of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, or 5.0% w/v, as well as in a range between any two of said polymer proportions. The formulations may comprise combinations of polymers, in amounts that individually or in aggregate achieve(s) the stated polymer proportions.

In some embodiments, formulations of the disclosure contain a surfactant. Surfactants useful in certain formulations of the disclosure include sodium lauryl sulfate, docusate sodium, phosphatidylcholine, lecithin, betaines, tyloxapol, polyoxyethylene sorbitan esters, such as polysorbate 20, polysorbate 60, and polysorbate 80; polyethoxylated castor oils, such as cremaphor, polyethoxylated hydrogenated castor oils, such as HCO-40; and poloxamers. Such surfactants may be present in formulations of the disclosure in weight to volume proportions of the overall formulation of 0.001% w/v, 0.005% w/v, 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, 1.0% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, or in a ranges between any two of said surfactant proportions. The formulations may comprise combinations of surfactants, in amounts that individually or in aggregate achieve(s) the stated weight to volume proportions.

In some embodiments, formulations of the disclosure can contain a tonicity agent. Ionic tonicity agents useful in certain formulations of the disclosure include calcium chloride, magnesium chloride, potassium chloride, sodium chloride, sodium sulfate, and combinations thereof. Nonionic tonicity agents useful in the formulations described herein include mannitol, sorbitol, xylitol, erythritol, lactitol, maltitol, isomalt, and combinations thereof. The formulations may comprise tonicity agent in weight to volume proportions of the overall formulation of 0.001% w/v, 0.005% w/v, 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, 1.0% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, or in a range between any two of said tonicity agent proportions. The formulations may comprise combinations of tonicity agent, in amounts that individually or in aggregate achieve(s) the stated tonicity weight to volume proportions.

In some embodiments, formulations of the disclosure can contain a preservative. Preservatives useful in certain formulations of the disclosure include dibutylhydroxytoluene, benzalkonium chloride, benzyl alcohol, borates, parabens, cresols, benzoic acid, phenol, sorbic acid, benzethonium chloride, sodium chlorite and combinations thereof. The formulations may comprise preservative in weight to volume proportions of the overall formulation of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, and 5.0% w/v, or in a range between any two of said preservative proportions. The formulations may comprise combinations of preservatives, in amounts that individually or in aggregate achieve(s) the stated weight to volume proportions.

EXAMPLES

Aspects of embodiments of the present disclosure may be further understood in light of the following examples, which should not be construed as limiting in any way. Objectives of the solubility and viscosity studies of the present disclosure were to evaluate the extent of apixaban solubility in a variety of liquid formulations.

EXAMPLE 1

Apixaban solubility. Aqueous apixaban formulations 0277-034A, 0277-034B, and 0277-034C comprised the ingredients set forth in Table 1.1 and were studied in the apixaban solubility experimental protocols described in this Example 1.

TABLE 1.1

| Apixaban formulations 0277-034A-C | | | |
|---|---|---|---|
| Ingredient | 0277-034A mg/ml | 0277-034B mg/ml | 0277-034C mg/ml |
| Apixaban | 3.0 | 3.0 | 3.0 |
| Glycerol | 1,260.0 | 1,260.0 | 1,260.0 |
| Total | 1,263.0 | 1,263.0 | 1,263.0 |

Apixaban batch manufacture. Formulations 0277-034A, 0277-034B, and 0277-034C were made as follows. Step 1: 126 g of glycerol was weighed into a glass beaker that had been zero tared to a laboratory scale. The glycerol was mixed with a magnetic stir rod and heated to 80° C.±5° C. in the glass beaker. Step 2: 300 mg of apixaban was weighed and slowly added to the 80° C. ±5° C. glycerol in the glass beaker from step 1, with continued stirring until the resulting suspension of apixaban in glycerol in the glass beaker reached 55° C. (at least one hour). Step 3: The resultant solution from Step 2 was cooled to room temperature (25° C.±2° C.) in the glass beaker and then sealed with parafilm and transferred to analytical for further processing in controlled solubility study and relevant analytical testing (assay on representative mixed sample as-is and assay on supernatant liquid after filtration).

Apixaban HPLC analytical testing. The analytical methods and sampling steps performed on formulations 0277-034A, 0277-034B, and 0277-034C were conducted at room temperature (25° C.±2° C.) and as set forth in Table 1.2.

TABLE 1.2

| Time point | Analytical methods and sampling steps |
| --- | --- |
| $T_0$ hours | a. 5-10 ml samples were collected from each of formulations 0277-034A, 0277-034B, and 0277-034C immediately after batch manufacture Step 3.<br>b. The apixaban HPLC assay was performed on each sample collected in $T_0$ hour Step a. "as is." The apixaban concentration (in mg/ml) for each sample was determined.<br>c. 1 ml of each $T_0$ hour Step a. sample was filtered through a 0.45-micron, PTFE filter and the filtrate was run in the apixaban HPLC assay. The apixaban concentration (in mg/ml) for each sample was determined. |
| $T_{12}$ hours | a. 5-10 ml samples were collected from each of formulations 0277-034A, 0277-034B, and 0277-034C 12 hours after batch manufacture Step 3.<br>b. The apixaban HPLC assay was performed on each sample collected in $T_{12}$ hour Step a. "as is." The apixaban concentration (in mg/ml) for each sample was determined.<br>c. 1 ml of each $T_{12}$ hour Step a. sample was filtered through a 0.45-micron, PTFE filter and the filtrate was run in the apixaban HPLC assay. The apixaban concentration (in mg/ml) for each sample was determined.<br>d. Filtration supernatant assay results were compared to $T_0$ results. |
| $T_{16}$ hours | a. 5-10 ml samples were collected from each of formulations 0277-034A, 0277-034B, and 0277-034C 16 hours after batch manufacture Step 3.<br>b. The apixaban HPLC assay was performed on each sample collected in $T_{16}$ hour Step a. "as is." The apixaban concentration (in mg/ml) for each sample was determined.<br>c. 1 ml of each $T_{16}$ hour Step a. sample was filtered through a 0.45-micron, PTFE filter and the filtrate was run in the apixaban HPLC assay. The apixaban concentration (in mg/ml) for each sample was determined.<br>d. Filtration supernatant assay results were compared to $T_{12}$ results, if any result within +5% of $T_{12}$ was observed it was reported to formulator. |
| $T_{20}$ hours | a. 5-10 ml samples were collected from each of formulations 0277-034A, 0277-034B, and 0277-034C 20 hours after batch manufacture Step 3.<br>b. The apixaban HPLC assay was performed on each sample collected in $T_{20}$ hour Step a. "as is." The apixaban concentration (in mg/ml) for each sample was determined.<br>c. 1 ml of each $T_{20}$ hour Step a. sample was filtered through a 0.45-micron, PTFE filter and the filtrate was run in the apixaban HPLC assay. The apixaban concentration (in mg/ml) for each sample was determined.<br>d. Filtration supernatant assay results were compared to $T_{16}$ results, if any result within +5% of $T_{16}$ was observed it was reported to the formulator. |
| $T_{24}$ hours | a. 5-10 ml samples were collected from each of formulations 0277-034A, 0277-034B, and 0277-034C immediately after batch manufacture Step 3.<br>b. The apixaban HPLC assay was performed on each sample collected in $T_{24}$ hour Step a. "as is." The apixaban concentration (in mg/ml) for each sample was determined.<br>c. 1 ml of each $T_{24}$ hour Step a. sample was filtered through a 0.45-micron, PTFE filter and the filtrate was run in the apixaban HPLC assay. The apixaban concentration (in mg/ml) for each sample was determined.<br>d. Filtration supernatant assay results were compared to $T_{20}$ results, if any result within +5% of $T_{20}$ was observed it was reported to the formulator. |

The solutions, standards, and samples used in the apixaban assay analytical methods of the present disclosure were as described in Table 1.2.

TABLE 1.2

Apixaban assay solutions and sample preparation

| | |
|---|---|
| Mobile phase A: | 2.31 g of ammonium acetate was weighed and transferred to a 1000 ml volumetric flask and made up to 1000 ml with purified water. Adjust the pH using glacial acetic acid to 4.7 ± 0.05 and mix well. Filter the buffer solution through 0.45 μ membrane filter. |
| Mobile phase B: | 900 ml of acetonitrile were measured and transferred to a 1000 ml volumetric flask. 100 ml of purified water and 1 ml of glacial acetic acid were measured and transferred into the flask, then mixed well and degassed for 30 minutes. |
| Diluent: | 500 ml of acetonitrile and 500 ml of water were measured and transferred into a bottle, mixed well, and degassed for 30 minutes. |
| Column wash A: | 200 ml of acetonitrile and 800 ml of water were measured and transferred into a bottle, mixed well, and degassed for 30 minutes. |
| Column wash B: | 800 ml of acetonitrile and 200 ml of water were measured and transferred into a bottle, mixed well, and degassed for 30 minutes. |
| Assay standard solution: | 10 mg of apixaban working standard were weighed and transferred into a 100 ml volumetric flask. 60 to 70 ml of diluent was then added into the flask, and the resultant liquid was sonicated to dissolve the content completely. Diluent was then added to a final volume of 100 ml. Approximate apixaban concentration: 0.1 mg/ml. |
| Assay standard check solution: | 10 mg of Apixaban working standard were weighed and transferred into a 100 ml volumetric flask. 60 to 70 ml of diluent was then added into the flask, and the resultant liquid was sonicated to dissolve the content completely. Diluent was then added to a final volume of 100 ml. Approximate apixaban concentration: 0.1 mg/ml. |
| Assay sample preparation - apixaban: | 10 mg of apixaban were weighed and transferred into a 100 ml volumetric flask. 60 to 70 ml of diluent was then added into the flask, and the resultant liquid was sonicated to dissolve the content completely. Dilute to volume with diluent and mixed well. Diluent was then added to a final volume of 100 ml. Approximate apixaban concentration: 0.1 mg/ml. |
| Assay sample preparation - finished formulations: | As is sample: The formulation was mixed to uniformity with a stir bar for 2-3 minutes and a 1 ml of sample of the mixed formulation was pipetted with a micropipette into a 20 ml volumetric flask and the 1 ml sample was then diluted to a final volume of 20 ml with diluent. Approximate apixaban concentration: Apixaban 0.1 mg/ml.<br>Filtrate fraction: Either: (i) the formulation was centrifuged at 5000 rpm for 20 min in an ultracentrifuge and the clear supernatant was collected; or (ii) in case a clear supernatant was not achieved with ultracentrifugation, the formulation was filtered with a 0.45 μm, PTFE filter. Then, 1 ml of either (i) clear supernatant or (ii) filtrate was pipetted with a micropipette into a 20 ml volumetric flask and diluted to a final volume of 20 ml with diluent. Approximate apixaban concentration: Apixaban 0.1 mg/ml. |

The chromatographic conditions for the apixaban high performance liquid chromatography ("HPLC") assay employed in the present disclosure were as forth in Table 1.3.

TABLE 1.3

Apixaban HPLC chromatographic parameters

| Chromatographic parameters | Equipment and/or conditions | | |
|---|---|---|---|
| System | HPLC equipped with variable wavelength and/or PDA (DAD) detector, column heater/chiller, and binary or a tertiary solvent pump | | |
| Column | Luna Phenyl hexyl, 150 mm × 4.6 mm, 3 μm | | |
| Column Temperature | 25° C. | | |
| Sample Tray Temperature | Ambient | | |
| Detector Wavelength | UV 210 nm | | |
| Pump Mode | Gradient | | |
| Flow Rate | 8.0 ml/min | | |
| Injection Volume | 10 μl | | |
| Apixaban retention time | About 4.6 min | | |
| Run Time | 15 minutes | | |
| | Time (min) | Mobile phase A% | Mobile phase B% |
| Gradient | 0 | 55 | 45 |
| | 3 | 55 | 45 |
| | 10 | 20 | 80 |
| | 11 | 55 | 45 |
| | 15 | 55 | 45 |
| Column wash solutions | Acetonitrile: water = 10:90 v/v and followed by Acetonitrile: water = 90:10 v/v | | |

The HPLC system was equilibrated with mobile phase for about 30 minutes. Iterative injections of diluent were made until a clean and reproducible baseline was achieved. The chromatograms were recorded and any peak eluting at the retention time of major peaks identified. Five replicate injections of apixaban working standard solution were made and chromatograms recorded. The average and relative standard deviation (% RSD) for the apixaban peak area responses were calculated from the five replicate injections of the apixaban working standard solution.

Two replicate injections of assay standard check solution were made and chromatograms recorded. The average peak area responses of the apixaban obtained from the two replicate injections of standard check solution were calculated and then the similarity factor was calculated. One injection of diluent was made before injecting each sample solutions. One injection of each sample solution was made, chromatogram recorded, and the apixaban peak area determined. The apixaban concentration in each sample solution was calculated. After six injections of sample solution and at the end of the sequence, one injection of diluent was made followed by one injection of working standard solution (bracketing). The % RSD of apixaban peak area obtained from the initial five injections of working standards and bracketing standard.

The equation employed to calculate percent assay for apixaban in the samples of the formulations of the present disclosure are set forth in Table 1.4.

TABLE 1.4

Apixaban HPLC assay equations

Assay for apixaban (on dried basis)

$$\% \text{ Assay} = \frac{Aspl}{Astd} \times \frac{Wstd}{100 \text{ mL}} \times \frac{\% \, Pstd}{100\%} \times \frac{100 - \% \, LOD \, std}{100\%} \times \frac{100 \text{ mL}}{Wspl} \times \frac{100}{Pspl} \times \frac{100\%}{100 - \% \, LOD \, spl} \times 100\%$$

Assay for apixaban (in finished formulation)

$$\% \text{ Assay} = \frac{Aspl}{Astd} \times \frac{Wstd}{100 \text{ mL}} \times \frac{\% \, Pstd}{100\%} \times \frac{100 - \% \, LOD \, std}{100\%} \times \frac{20 \text{ mL}}{1 \text{ ml}} \times \frac{1}{LC} \times 100\%$$

Assay for apixaban (in soluble fraction (mg/ml) of finished formulation)

$$\text{Soluble fraction} = \frac{Aspl}{Astd} \times Std. \, conc \times \frac{20 \text{ ml}}{1 \text{ ml}}$$

$$Std. \, conc \left(\frac{mg}{mL}\right) = \frac{Wstd}{100 \text{ mL}} \times \frac{\% \, Pstd}{100\%} \times \frac{100 - \% \, LOD \, std}{100\%}$$

Where:
| | |
|---|---|
| Astd | Average peak area of apixaban from first 5 replicate standards injections |
| Aspl | Peak Area of apixaban from sample injection |
| Wstd | Weight of apixaban used to prepare standard |
| Wspl | Weight of apixaban used to prepare sample |
| % Pstd | Percentage purity of apixaban in working standard |
| % Pspl | Percentage purity of apixaban in sample |
| %LOD std | % Loss on drying of Apixaban standard |
| %LOD spl | % Loss on drying of Apixaban sample |

The HPLC assay experimental results for formulation 0277-034A, 0277-034B, and 0277-034C are reported in Table 1.5.

TABLE 1.5

Solubility of formulations 0277-034A, 0277-034B, and 0277-034C determined by HPLC assay

| Time (hours) | Test | 0277-034A | 0277-034B | 0277-034C | Average |
|---|---|---|---|---|---|
| $T_0$ | As Is assay (mg/ml) | 2.92 | 2.90 | 2.87 | 2.90 |
| | Supernatant (a) (mg/ml) | 2.02 | 2.39 | 2.12 | 2.18 |
| $T_{12}$ | Supernatant (b) (mg/ml) | 1.67 | 2.42 | 1.82 | 1.97 |
| | % Difference (a)-(b)/(a)*100 | 17.25 | −1.49 | 14.20 | 10.48 |
| $T_{16}$ | Supernatant (c) (mg/ml) | 1.49 | 1.99 | 1.70 | 1.72 |
| | % Difference (b)-(c)/(b)*100 | 10.87 | 18.06 | 6.82 | 11.92 |
| $T_{20}$ | Supernatant (d) (mg/ml) | 1.47 | 1.97 | 1.67 | 1.71 |
| | % Difference (c)-(d)/(c)*100 | 1.34 | 1.02 | 0.76 | 1.04 |
| $T_{24}$ | Supernatant (e) (mg/ml) | 1.41 | 1.89 | 1.65 | 1.65 |
| | % Difference (d)-(e)/(d)*100 | 4.08 | 3.97 | 2.14 | 3.39 |

*Since the value is negative, the value taken is 0.

While the foregoing specification teaches the principles of the present invention, with examples provided for the purpose of illustration, it will be understood that the practice of the invention encompasses all variations, adaptations and/or modifications as come within the scope of the following claims and their equivalents.

What is claimed is:

1. A liquid pharmaceutical formulation, suitable for oral administration, that comprises:
   a therapeutically effective amount of apixaban; and
   an amount of glycerol sufficient to result in from 0.75 mg/ml to 1.75 mg/ml of the apixaban being in the solution phase of the formulation, at 20 hours after the formulation's manufacture when the formulation is kept at 25° C.±2° C.;
   wherein the formulation is free of added:
   polysorbate, poloxamer, polyoxyethylene castor oil, a polyoxyglyceride, vitamin E polyethylene glycol succinate, macrogol 15 hydroxy stearate, sodium lauryl sulfate, and docusate sodium;
   povidone, hydroxypropyl cellulose, and hydroxypropyl methylcellulose;
   propylene glycol, sorbitol, and mannitol; and
   fructose, sucrose, and lactose.

2. The formulation of claim 1, wherein the amount of apixaban in the solution phase of the formulation is from 0.75 mg/ml to 1.75 mg/ml.

3. The formulation of claim 1, wherein the amount of apixaban in the solution phase of the formulation is from 1.0 mg/ml to 1.75 mg/ml.

4. The formulation of claim 1, wherein the amount of apixaban in the solution phase of the formulation is 1.0 mg/ml.

5. The formulation of claim 1, wherein the amount of glycerol is from 370 mg/ml to 1260 mg/ml.

6. The formulation of claim 2, wherein the amount of glycerol is from 462.5 mg/ml to 1260 mg/ml.

7. The formulation of claim 3, wherein the amount of glycerol is from 740 mg/ml to 1260 mg/ml.

8. The formulation of claim 4, wherein the amount of glycerol is 1260 mg/ml.

9. The formulation of claim 1, wherein the formulation is free of added surfactant, hydrophilic polymer, polyhydric alcohol other than the glycerol, and carbohydrate.

10. A method of (i) reducing the risk of stroke and systemic embolism in patients with nonvalvular atrial fibrillation, (ii) reducing the risk of deep vein thrombosis leading to pulmonary embolism in patients who have undergone hip or knee replacement surgery, (iii) treating deep vein thrombosis and pulmonary embolism, or (iv) treating recurrent deep vein thrombosis and pulmonary embolism, comprising orally administering the formulation of claim 1 to a subject presenting nonvalvular atrial fibrillation, deep vein thrombosis or pulmonary embolism or who has undergone hip or knee replacement therapy.

11. The method of claim 10, wherein the formulation is administered to the subject once daily and wherein the formulation comprises a total amount of apixaban of from 1 mg to 10 mg.

* * * * *